United States Patent [19]
Pagay et al.

[11] Patent Number: 5,330,759
[45] Date of Patent: Jul. 19, 1994

[54] ENTERIC COATED SOFT CAPSULES AND METHOD OF PREPARATION THEREOF

[75] Inventors: Shrikant N. Pagay, Guilderland; Gregg Stetsko, Bethlehem, both of N.Y.

[73] Assignee: Sterling Winthrop Inc., New York, N.Y.

[21] Appl. No.: 935,505

[22] Filed: Aug. 26, 1992

[51] Int. Cl.$^5$ ................................................ A61K 9/58
[52] U.S. Cl. ..................................... 424/462; 424/452; 424/463
[58] Field of Search ................ 424/456, 452, 462, 463

[56] References Cited

U.S. PATENT DOCUMENTS

| | | | |
|---|---|---|---|
| 4,816,259 | 3/1989 | Matthews et al. | 424/463 |
| 5,047,258 | 9/1991 | Belanger et al. | 427/3 |

OTHER PUBLICATIONS

Röhm Pharma product brochure entitled "Eudragit L30D" (Info LD-1/e, pp. 1-7, and Info LD-2/e, two pages).

Primary Examiner—Paul R. Michl
Assistant Examiner—Jyothsna Venkat
Attorney, Agent, or Firm—Richard A. Hake; Paul E. Dupont; Theodore C. Miller

[57] ABSTRACT

Soft capsules coated with an enteric coating comprising a 1:1 copolymer of methacrylic acid and methyl or ethyl acrylate or methyl or ethyl methacrylate and a plasticizer without need for a subcoating and optionally additionally coated with a protective coating comprising hydroxypropyl methylcellulose or hydroxypropyl cellulose or a mixture thereof and a plasticizer and method of preparation thereof are disclosed.

7 Claims, No Drawings

ENTERIC COATED SOFT CAPSULES AND METHOD OF PREPARATION THEREOF

BACKGROUND OF THE INVENTION

1. Field of the Invention

The invention relates to soft capsules coated with an enteric coating without need for a subcoating and optionally additionally coated with a protective coating and method of preparation thereof.

2. Information Disclosure Statement

Enteric coating of soft capsules has heretofore required a glidant such as talc to prevent agglomeration of the capsules and a subcoating to stiffen the capsules and thereby prevent distortion thereof during coating. The prior art does not describe or suggest any means of overcoming either problem. The presently described and claimed invention overcomes both of them.

A Röhm Pharma product brochure entitled "Eudragit L 30 D—Aqueous Acrylic Resin Dispersion—Application in the Production of Pharmaceutical Preparations" (Info LD-1/e, pages 1-7 and Info LD-2/e, two pages) describes EUDRAGIT L 30 D and use thereof as follows:

EUDRAGIT L 30 D is utilised predominantly for covering orally administered pharmaceutical dosage forms, particularly tablets, pills and capsules, with coatings which are resistant to gastric juice but soluble in intestinal juice.

EUDRAGIT L 30 D is a copolymer, anionic in character, based on polymethylacrylic acid and acrylic acid esters.

The ratio of the free carboxyl groups to the ester groups is 1:1.

The mean molecular weight is 250 000.

EUDRAGIT L 30 D is supplied as an aqueous dispersion containing 30% w/w of dry lacquer substance.

To achieve coatings which are resistant to gastric juice, it is necessary to apply lacquer containing 3 to 6 mg of dry substance per sq. cm of tablet surface. For enteric coatings with delayed drug release in the intestine, larger quantities of lacquer will possibly need to be applied. In certain cases, EUDRAGIT L 30 D containing 30% w/w of dry lacquer substance can be employed undiluted, possibly for granulation purposes, to isolate porous cores or in fraction application.

Uniform and smooth film coatings are obtained by spray application; this process requires that the dispersion be diluted to some 20% w/w with water. To enhance the elasticity of the EUDRAGIT L 30 D films, the addition of plasticisers is strongly recommended. Polyethylene glycols, propylene glycol, triacetin and dibutyl phthalate, citric acid esters have proved suitable as plasticisers. The addition of 10% w/w of plasticiser, calculated on the dry lacquer substance content, is generally adequate. Where required, this can be increased to 20-25% without adversely affecting the specific solubility characteristics of the lacquer film. The addition of a small quantity of talc reduces the tendency of EUDRAGIT L 30 D to agglutinate during the application process and helps to make the surface of the film smooth. Belanger et al. U.S. Pat. No. 5,047,258, which issued Sep. 10, 1991, describes

[a] method of preventing pharmaceutical dosage forms from adhering during spray coating, comprising: spraying said pharmaceutical dosage forms in the absence of glidant [especially talc] with a mixture consisting essentially of a one to one copolymer of ethyl acrylate and methacrylic acid and a plasticizer in air having an inlet dew point below about 10° C. and an inlet temperature between about 35° C. and about 60° C.

The term "pharmaceutical dosage forms" is not explicitly defined. The specification states that the invention relates to a process for the spray-coating of "tablets, pills, and the like" and illustrates the invention only by tablets in the examples.

Matthews et al. U.S. Pat. No. 4,816,259, which issued Mar. 28, 1989, describes a process for making coated soft gelatin capsules including enteric coated soft gelatin capsules comprising first coating the capsule shell with a subcoating composition consisting essentially of hydroxypropyl methyl cellulose about 4%-9%, polyethylene glycol about 0.5%-1% with the remainder water in an [a]mount sufficient to increase the total weight of said shell by about 8%-10%, and thereafter applying one or more continuous coating layers to said shell comprising a known hard tablet coating composition selected from the group consisting of: waterproofing and sealing compounds, smoothing compounds, coloring and finishing compounds, polishing compounds, cellulose polymer film compositions, compression coating compositions, and enteric coating compounds, wherein said subcoating is applied to said capsule shell using standard spraying techniques at a temperature below the distortion temperature of the capsule shell thereby essentially eliminating deformation of the capsule shell during the manufacturing process and capsules prepared by the process. The preferred enteric coating composition is 12-18% of polyvinyl acetate phthalate, 0.25-0.35% concentrated ammonium hydroxide and water to make 100%.

SUMMARY OF THE INVENTION

In a first composition of matter aspect the invention is a filled soft capsule not having a subcoating and coated with from about 1 to about 20 mg./cm.$^2$ of an enteric coating consisting essentially of by weight from about 60% to about 90% of a 1:1 copolymer of methacrylic acid and methyl or ethyl acrylate or methyl or ethyl methacrylate and from about 10% to about 40% of a plasticizer selected from the group consisting of triacetin, a polyethylene glycol having a molecular weight in the range from 400 to 3350, propylene glycol, dibutyl phthalate and triethyl citrate or mixture thereof.

In a second composition of matter aspect the invention is a capsule in accordance with the first composition of matter aspect of the invention additionally coated with from about 1 to about 10 mg./cm.$^2$ of a protective coating consisting essentially of by weight from about 60% to about 90% of a cellulose derivative which is hydroxypropyl methylcellulose or hydroxypropyl cellulose or a mixture thereof and from about 10% to about 40% of a plasticizer selected from the group consisting of triacetin, a polyethylene glycol having a molecular weight in the range from 400 to 3350, propylene glycol, dibutyl phthalate, triethyl citrate, glycerin and diacetylated monoglycerides or a mixture thereof.

In a first process aspect the invention is the process of preparing a capsule in accordance with the first composition of matter aspect of the invention which comprises mixing the 1:1 copolymer of methacrylic acid and methyl or ethyl acrylate or methyl or ethyl methacrylate and the plasticizer in from about 2 times to about 8 times the combined weight thereof of water, spraying a filled soft capsule not having a subcoating using air at a temperature in the range from 30° C. to 60° C. with the resulting mixture in sufficient amount to produce from about 1 to about 20 mg./cm.$^2$ of enteric coating on the capsule after drying, and then drying the capsule with air at a temperature in the range from 30° C. to 60° C.

In a second process aspect the invention is the process of preparing a capsule in accordance with the second composition of matter aspect of the invention which comprises mixing the hydroxypropyl methylcellulose or hydroxypropyl cellulose or mixture thereof and the plasticizer in from about 5 to about 15 times the combined weight thereof of water, spraying a capsule prepared in accordance with the first process aspect of the invention using air at a temperature in the range from 30° C. to 60° C. with the resulting mixture in sufficient amount to produce from about 1 to about 10 mg./cm.$^2$ of protective coating on the capsule after drying, and then drying the capsule with air at a temperature in the range from 30° C. to 60° C.

DETAILED DESCRIPTION OF THE INVENTION

Enteric coated soft gelatin capsules of the prior art have needed a subcoating to stiffen them and thereby to prevent distortion during the coating process, which has been carried out at or above the distortion temperature (65°–75° C.). The manufacturer of the 1:1 copolymer of methacrylic acid and methyl or ethyl acrylate or methyl or ethyl methacrylate has recommended that due to its tacky nature an agent such as talc be used to prevent adherence of capsules during the coating process. Talc however tends to clog the spray nozzles used in the coating process. The invention overcomes both of these problems by allowing use of a coating temperature below the distortion temperature of the capsules and thereby avoiding use of subcoated capsules and allowing omission of an antiadherent agent in the coating process and thereby avoiding clogged spray nozzles.

The soft capsule shell of the composition of matter aspects of the invention can be any pharmaceutically acceptable soft capsule shell but is preferably a soft gelatin capsule shell and is of suitable size for containing from about 40 milligrams or about 0.04 milliliter to about 800 milligrams or about 0.8 milliliter of filling. Soft gelatin capsule shells are commercially available and generally contain in addition to gelatin a plasticizer, a preservative and a colorant. Conventional machinery and technique are used in filling the soft capsule shells.

The capsule filling can be any liquid, solid or semi-solid pharmaceutical composition suitable for oral administration but is preferably a liquid or semi-solid composition since soft capsules, which are more expensive to make than hard capsules, are generally used when a pharmaceutical substance cannot be formulated as a solid. Pharmaceutical substance means any drug for treating or preventing any disease or disorder or mixture thereof or any nutritional aid. A pharmaceutical substance used to illustrate the invention is an antiviral agent described by Diana U.S. Pat. No. 4,843,087 issued Jun. 27, 1989, which is the compound described as 5-{5-[2,6-dichloro-4-(4,5-dihydro-2-oxazolyl)phenoxy]pentyl}-3-methylisoxazole in part (c) of example 105 thereof and which cannot be formulated as a solid. The amount of pharmaceutical substance in the capsule filling depends on the dose needed. A drug for treating or preventing a disease or disorder can constitute from as little as 0.1% to as much as 90% by weight of the capsule filling. A nutritional aid, for example garlic oil, can constitute the entire capsule filling. Conventional excipients, if any, constitute the remainder of the capsule filling, which is prepared using conventional equipment and methods.

The excipients used to prepare the capsule filling and the substances used to prepare the enteric coating and the protective coating of the invention are known pharmaceutical ingredients and are described by manufacturers's product brochures and pharmaceutical texts, for example The United States Pharmacopeia, Twenty-second Revision and The National Formulary, Seventeenth Edition (a single volume also entitled 1990 USP XXII NF XVII; copyright by United States Pharmacopeial Conventional, Inc., 12601 Twinbrook Parkway, Rockville, Md 20852, 1989). A set of monographs is presented and arranged alphabetically by name in each of the United States Pharmacopeial (USP) and National Formulary (NF) sections thereof. The conventional followed thereby in naming the substances described is that the first letter of each word of the name is capitalized. The substances used to prepare the below-described example are described under the following names (section, page(s)): Hydroxypropyl Methylcellulose (USP, pp. 670–671), Triacetin (USP, p. 1392), Methacrylic Acid Copolymer (NF, pp. 1946–1947), Polyethylene Glycol (NF, pp. 1961–1963), Polysorbate 80 (NF, p. 1968).

Hydroxypropyl Methylcellulose is described as "[c]ellulose, 2-hydroxypropyl methyl ether" and as "a propylene glycol ether of methylcellulose". When dried it contains "methoxy (OCH$_3$) and hydroxypropoxy (OCH$_2$CHOHCH$_3$) groups" conforming to certain limits. Hydroxypropyl Methylcellulose 2910 for example has a minimum of 28.0% and a maximum of 30.0% of methoxy groups and a minimum of 7.0% and a maximum of 12.0% of hydroxypropoxy groups.

Triacetin is described as well by the names "1,2,3-[p]ropanetriol triacetate" and "[g]lycerin triacetate" and by the structural formula

Methacrylic Acid Copolymer is described as "a fully polymerized copolymer of methacrylic acid and an acrylic or methacrylic ester." Types A, B and C are specifically described in terms of percent methacrylic acid units and visocity units. Type C is specified as having a methacrylic acid content of 46.0–50.6% and a viscosity of 100–200 cps and is the dry polymer corresponding to the aqueous dispersion thereof described as EUDRAGITL 30 D by the above-cited Röhm Pharma product brochure.

Polyethylene Glycol is described as "an addition polymer of ethylene oxide and water, represented by the formula

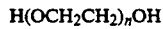

in which n represents the average number of oxyethylene groups." The variants are designated by "nominal value" of "average molecular weight". Polyethylene glycols having nominal average molecular weights in the range from 300 to 8000 are described. Polyethylene Glycol 600 and Polyethylene Glycol 1000 were used to prepare the below-described example.

Polysorbate 80 is described as a poly(oxy-1,2-ethanediyl) derivative of sorbitan mono-9-octadecenoate, as "an oleate ester of sorbitol and its anhydrides copolymerized with approximately 20 moles of ethylene oxide for each mole of sorbitol and sorbitol anhydrides", and as "[p]olyoxyethylene 20 sorbitan monooleate".

The mixing, spraying and drying steps of the process aspects of the invention are carried out using conventional equipment. The 1:1 copolymer of methacrylic acid and methyl or ethyl acrylate or methyl or ethyl methacrylate, plasticizer and water of the first process aspect of the invention are preferably mixed at room temperature. The hydroxypropyl methylcellulose or hydroxypropyl cellulose or mixture thereof, plasticizer and water of the second process aspect of the invention are preferably mixed with warming, preferably to about 80° C., using part of the water and then cooled, preferably to room temperature, using the remainder of the water to complete the mixture and aid in cooling. Spraying is carried out with batches of capsules in a coating pan using one or more spray nozzles with warm air flow to remove water from the coated capsules as the coating proceeds. The inlet air temperature is in the above-stated range from 30° C. to 60° C., preferably from 40° C. to 50° C. The amount of enteric coating applied to the capsules as stated above is from about 1 to about 20 mg./cm.$^2$, preferably from about 5 to about 15 mg./cm.$^2$ and most preferably from about 8 to about 12 mg./cm.$^2$. The relative weight of the 1:1 copolymer of methacrylic acid and methyl or ethyl acrylate or methyl or ethyl methacrylate in the enteric coating is as stated above from about 60% to about 90% thereof and is preferably from about 75% to about 85% thereof. The relative weight of plasticizer in the enteric coating is as stated above from about 10% to about 40% thereof and is preferably from about 15% to about 25% thereof. The amount of protective coating as stated above is from about 1 to about 10 mg./cm.$^2$, preferably from about 2 to about 4 mg./cm.$^2$. The relative weight of hydroxypropyl methylcellulose or hydroxypropyl cellulose or mixture thereof in the protective coating is as stated above from about 60% to about 90% thereof and is preferably from about 75% to about 85% thereof. The relative weight of plasticizer in the protective coating is as stated above from about 10% to about 40% thereof and is preferably from about 15% to about 25% thereof. After completion of spraying drying is preferably carried out in the same coating pan with the same warm air flow at the same inlet air temperature.

EXAMPLE

| Ingredient | Weight (kg.) | % by Weight |
|---|---|---|
| Capsule Filling | | |
| 5-{5-[2,6-Dichloro-4-(4,5-dihydro-2-oxazolyl)-phenoxy]pentyl}-3-methylisoxazole | 19.1 | 50.0 |
| Polyethylene Glycol 600 | 9.55 | 25.0 |
| Polyethylene Glycol 1000 | 7.64 | 20.0 |
| Polysorbate 80 | 1.91 | 5.00 |
| Total | 38.2 | 100.0 |

The two polyethylene glycols and the Polysorbate 80 were combined and heated with occasional stirring to 50° C. until the Polyethylene Glycol 1000 was melted. The 5-{5-[2,6-dichloro-4-(4,5-dihydro-2-oxazolyl)-phenoxy]pentyl}-3-methylisoxazole was added with heating and occasional mixing at 46° C. until the mixture was uniform (40 minutes). Heating was discontinued and occasional mixing was continued until the mixture congealed to an off-white, opaque semi-solid. The temperature was then 27° C. The mixture was filled with continuous mixing thereof at 27°–30° C. into soft gelatin capsules so that each filled capsule contained 206 milligrams of the mixture and weighed in total 350 milligrams.

| Ingredient | Weight (kg.) | Weight (mg./capsule) |
|---|---|---|
| Capsule Coating | | |
| Filled Capsules of this Example | 7.00 | 350. |
| Enteric Coating | | |
| Methacrylic Acid Copolymer (Type C, 30% Dispersion by Weight in Water) | 1.23 | 16.8 (dry) |
| Triacetin | 0.092 | 4.20 |
| Water | 0.988 | 0.0 |
| Protective Coating | | |
| Hydroxypropyl Methylcellulose 2910 | 0.123 | 5.60 |
| Triacetin | 0.031 | 1.40 |
| Water | 1.390 | 0.0 |
| Total | | 378. |

The weights in the left column include 10% overage for losses in carrying out the process steps. The weights in the right column are target weights. The 1:1 methacrylic acid-ethyl acrylate copolymer, triacetin and water for the enteric coating were mixed at room temperature. The hydroxypropyl methylcellulose, triacetin and about half the water for the protective coating were mixed with heating to 80° C., the remaining water was added, and the resulting solution was cooled to 25° C. The coatings were carried out in a twenty four-inch side-vented coating pan using a rotation rate of 14 r.p.m., two spray nozzles at atomizing air pressure of 60–65 p.s.i., a coating application rate of 40 ml./min., an inlet air temperature of 40°–44° C., an exhaust air temperature of 30°–34° C., a distance of 6.5 inches from nozzle to capsule bed, and water rinsing of the nozzles between coatings. The enteric coating time was approximately 60 minutes. The protective coating time was approximately 40 minutes. Drying was carried out at the same inlet and exhaust air temperatures. Drying time was 5 minutes. The capsules obtained were coated with 9 mg./cm.$^2$ of enteric coating and 3 mg./cm.$^2$ of protective coating.

We claim:

1. A filled soft capsule not having a subcoating and coated with from about 1 to about 20 mg./cm.$^2$ of an enteric coating consisting essentially of by weight from about 60% to about 90% of a 1:1 copolymer of methacrylic acid and methyl or ethyl acrylate or methyl or ethyl methacrylate and from about 10% to about 40% of a plasticizer selected from the group consisting of triacetin, a polyethylene glycol having a molecular weight in the range from 400 to 3350, propylene glycol, dibutyl phthalate and triethyl citrate and a mixture thereof.

2. A capsule according to claim 1 wherein the amount of enteric coating is from about 5 to about 15 mg./cm.$^2$.

3. A capsule according to claim 2 wherein the amount of enteric coating is from about 8 to about 12 mg./cm.$^2$.

4. A capsule according to claim 3 wherein the plasticizer is triacetin.

5. A capsule according to claim 4 wherein the relative weight of the 1:1 copolymer of methacrylic acid and methyl or ethyl acrylate or methyl or ethyl methacrylate in the enteric coating is from about 75% to about 85% thereof and the relative weight of triacetin in the enteric coating is from about 15% to about 25% thereof.

6. A capsule according to claim 5 wherein the capsule filling is a liquid or semi-solid composition containing a drug for treating or preventing a disease or disorder or mixture thereof or a nutritional aid.

7. A capsule according to claim 6 wherein the capsule filling is a semi-solid composition of 5-{5-[2,6-dichloro-4-(4,5-dihydro-2-oxazolyl)phenoxy]pentyl}-3-methylisoxazole, polyethylene glycol of molecular weight 600, polyethylene glycol of molecular weight 1000 and an oleate ester of sorbitol and sorbitol anhydrides copolymerized with approximately 20 moles of ethylene oxide for each mole of sorbitol and sorbitol anhydrides.

* * * * *